(12) United States Patent
Rosenberg et al.

(10) Patent No.: US 9,044,610 B2
(45) Date of Patent: Jun. 2, 2015

(54) SYSTEMS AND METHODS FOR PROVIDING A DISTRIBUTED VIRTUAL STIMULATION CATHODE FOR USE WITH AN IMPLANTABLE NEUROSTIMULATION SYSTEM

(71) Applicant: PACESETTER, INC., Sylmar, CA (US)

(72) Inventors: Stuart Rosenberg, Castaic, CA (US);
Martin Cholette, Action, CA (US);
Xiaoyi Min, Camarillo, CA (US)

(73) Assignee: PACESETTER, INC., Sylmar, CA (US)

( * ) Notice: Subject to any disclaimer, the term of this patent is extended or adjusted under 35 U.S.C. 154(b) by 137 days.

(21) Appl. No.: 13/850,088

(22) Filed: Mar. 25, 2013

(65) Prior Publication Data

US 2014/0277259 A1    Sep. 18, 2014

Related U.S. Application Data

(60) Provisional application No. 61/793,688, filed on Mar. 15, 2013.

(51) Int. Cl.
*A61N 1/36*    (2006.01)
*A61N 1/05*    (2006.01)

(52) U.S. Cl.
CPC ........... *A61N 1/36071* (2013.01); *A61N 1/0553* (2013.01)

(58) Field of Classification Search
CPC .................................................. A61N 1/36071
USPC .......................................................... 607/46
See application file for complete search history.

(56) References Cited

U.S. PATENT DOCUMENTS

| | | |
|---|---|---|
| 6,134,470 A | 10/2000 | Hartlaub |
| 6,937,896 B1 | 8/2005 | Kroll |
| 7,099,718 B1 | 8/2006 | Thacker et al. |
| 7,164,944 B1 | 1/2007 | Kroll et al. |
| 7,221,979 B2 | 5/2007 | Zhou et al. |
| 7,650,190 B2 | 1/2010 | Zhou et al. |
| 7,657,319 B2 | 2/2010 | Goetz et al. |
| 7,676,273 B2 | 3/2010 | Goetz et al. |
| 7,715,915 B1 | 5/2010 | Ryu et al. |
| 7,822,483 B2 | 10/2010 | Stone et al. |
| 7,826,899 B1 | 11/2010 | Ryu et al. |

(Continued)

FOREIGN PATENT DOCUMENTS

| | | |
|---|---|---|
| EP | 1991308 B1 | 4/2012 |
| EP | 1993663 B1 | 4/2012 |

(Continued)

*Primary Examiner* — Carl H Layno
*Assistant Examiner* — Jennifer Ghand

(57) ABSTRACT

Techniques are provided for controlling and delivering spinal cord stimulation (SCS) or other forms of neurostimulation. In one example, neurostimulation pulses are generated wherein successive pulses alternate in polarity so that a pair of electrodes alternate as cathodes. Each pulse has a cathodic amplitude sufficient to achieve cathodic capture of tissues adjacent the particular electrode used as the cathode for the pulse. The neurostimulation pulses are delivered to patient tissues using the electrodes to alternatingly capture tissues adjacent opposing electrodes via cathodic capture to achieve a distributed virtual stimulation cathode. Various pulse energy savings techniques are also set forth that exploit the distributed virtual stimulation cathode.

20 Claims, 11 Drawing Sheets

(56) References Cited

U.S. PATENT DOCUMENTS

| | | | |
|---|---|---|---|
| 7,826,902 B2 | 11/2010 | Stone et al. | |
| 7,848,802 B2 | 12/2010 | Goetz et al. | |
| 7,848,806 B1* | 12/2010 | Kroll | 607/8 |
| 7,860,563 B2 | 12/2010 | Foreman et al. | |
| 7,974,693 B2 | 7/2011 | Ben-David et al. | |
| 8,095,221 B2 | 1/2012 | Varrichio et al. | |
| 2007/0179579 A1* | 8/2007 | Feler et al. | 607/117 |
| 2007/0191895 A1 | 8/2007 | Foreman et al. | |
| 2007/0203537 A1 | 8/2007 | Goetz et al. | |
| 2007/0203543 A1 | 8/2007 | Stone et al. | |
| 2007/0203544 A1 | 8/2007 | Goetz et al. | |
| 2010/0057158 A1 | 3/2010 | Rodriguez et al. | |
| 2010/0076535 A1* | 3/2010 | Pianca et al. | 607/116 |
| 2010/0114207 A1 | 5/2010 | Snell et al. | |
| 2010/0114227 A1 | 5/2010 | Cholette | |
| 2010/0161006 A1 | 6/2010 | Keel et al. | |
| 2010/0268298 A1* | 10/2010 | Moffitt et al. | 607/45 |
| 2010/0312128 A1 | 12/2010 | Karst et al. | |
| 2010/0331921 A1 | 12/2010 | Bornzin et al. | |
| 2011/0130818 A1 | 6/2011 | Chen | |
| 2011/0137362 A1 | 6/2011 | Foreman et al. | |
| 2014/0107719 A1* | 4/2014 | Bornzin et al. | 607/9 |

FOREIGN PATENT DOCUMENTS

| | | |
|---|---|---|
| EP | 1993665 B1 | 4/2012 |
| WO | 2007097858 A1 | 8/2007 |
| WO | 2007097859 A1 | 8/2007 |
| WO | 2007097860 A1 | 8/2007 |
| WO | 2007097861 A1 | 8/2007 |
| WO | 2007097873 A1 | 8/2007 |
| WO | 2007100427 A1 | 9/2007 |

* cited by examiner

SYSTEMS AND METHODS FOR PROVIDING A DISTRIBUTED VIRTUAL STIMULATION CATHODE FOR USE WITH AN IMPLANTABLE NEUROSTIMULATION SYSTEM

RELATED APPLICATIONS

This application claims the benefit of U.S. Provisional Patent Application Ser. No. 61/793,688, filed Mar. 15, 2013, entitled "Systems and Methods for Providing a Distributed Virtual Stimulation Cathode for Use With an Implantable Neurostimulation System," which is fully incorporated by reference herein.

FIELD OF THE INVENTION

The invention generally relates to implantable neurostimulation systems such as spinal cord stimulation (SCS) systems and, in particular, to techniques for controlling the stimulation generated by such systems.

BACKGROUND OF THE INVENTION

SCS is a type of neurostimulation primarily intended to manage chronic pain, particularly within the back, neck, arms or legs. Benefits of SCS or other forms of neurostimulation may include: a reduction in pain; a reduction or elimination of the use of pain medications; and increased activity levels and an improved overall quality of life. Neurostimulation has been used to manage pain from failed back surgery syndrome or post-laminectomy syndrome and other neuropathies. To this end, an SCS system may be implanted within the body to deliver electrical pulses to nerves along the spinal cord. Some patients describe the resulting sensation as a gentle massaging sensation or, in some cases, simply the absence of pain. The SCS system typically includes a small generator device similar to a pacemaker but equipped to send electrical pulses to leads mounted along the nerves near the spinal cord. The generator is usually implanted in the abdomen or buttock area. The stimulation leads may include, e.g., thin wires or paddles for delivering electrical pulses to the nerves along the spinal cord. Thin wire leads, also referred to as percutaneous leads, may be implanted within the epidural space. Paddle leads are instead typically implanted during a surgical procedure where a small amount of bone is removed from one of the vertebra. An external controller, similar to a remote control device, is provided to allow the patient to control or adjust the neurostimulation.

SCS devices and other neurostimulators may be programmed or controlled using one or more stimulation sets or "Stim Sets." The stimulation sets specify the particular electrodes to be used as cathodes and anodes, as well as the pulse amplitude, pulse width and pulse frequency, and may further specify the duration and timing of the stimulation (i.e., the "dosage" specified, e.g., as "continuously running vs. a specified on/off cycle" or specified as a duration of a bolus followed by a minimum refractory period before the next bolus). SCS devices typically use a single stimulation set to capture neural structures at one anatomic location, or multiple stimulation sets that run simultaneously (interleaved) to achieve stimulation at multiple neural structures/anatomic locations. For example, programming an SCS system to cover a complex pain syndrome may require two stimulation sets to adequately treat knee and thigh pain, a third stimulation set to treat hip pain, and fourth and fifth stimulation sets to treat bilateral low back pain. Further, multiple stimulation sets may be used to adequately cover a broader region of pain without causing undesirable collateral stimulation of non-painful neighboring regions.

FIG. 1 illustrates the effect of a pair of stimulation sets (Stim Set 1 and Stim Set 2) configured to deliver interleaved sequences of biphasic pulses (sequences 2 and 4) using multiple electrodes of a percutaneous lead 5 to achieve stimulation at both a middle location 6 and a distal location 8 along the lead in accordance with at least some prior art techniques. In the figure, pulse sequence 2 generated by the first stimulation set is shown in sold lines along with the vectors used for that set. Pulse sequence 4 generated by the second stimulation set is shown in phantom lines along with the vectors used for that set. For Stim Set 1, pulses are either delivered between the two most distal of the electrodes of the lead or between a distal electrode and a middle electrode. In contrast, for Stim Set 2, pulses are either delivered between two of the middle electrodes or between one middle electrode and a distal electrode. In this manner, cathodic stimulation is achieved both at the distal end 8 of the lead and at the middle location 6, albeit with the complexity of requiring two stimulation sets. Note that, alternatively, the SCS device might try to exploit both anodal and cathodal stimulation (with cathodal stimulation at a distal electrode and anodal stimulation at a middle electrode) but anodal stimulation thresholds are two to three times higher than cathodal thresholds for neural stimulation. As such, to achieve anodal stimulation to deliver dual-site capture, much higher pulse amplitudes would be required, draining power and potentially causing unwanted accessory stimulation.

To provide cathodic stimulation to additional locations along the lead, more stimulation sets can be employed to specify additional and more densely interleaved pulse sequences. In addition to requiring more complex programming by the user (i.e. the clinician), multiple stimulation sets will tend to draw increased current from the implantable pulse generator (IPG) battery. In this regard, as the number of interleaved pulses increases so does the effective frequency from the IPG's single current source. As frequency increases, the device switches from passive discharge to active discharge, further draining energy while not contributing to additional neurophysiologic effects. These issues may become even more problematic within neurostimulation systems used to treat cardiac disorders such as heart failure or arrhythmia (such as SCS to reduce heart rate or blood pressure, protect against ischemic signaling transduction outside of ischemic areas, modulate coronary circulation, modulate local and regional refractoriness, etc.) To achieve the needed stimulation at various locations along the cervical and thoracic spine to achieve these cardioprotective effects, still more complex SCS stimulation sets may be required, resulting in even greater current drain and programming complexity.

Accordingly, it would be desirable to provide techniques for achieving efficient multi-site neurostimulation at reduced current drain. It is to these ends that aspects of the invention are generally directed.

SUMMARY

In an exemplary embodiment, a method is provided for use with an implantable system for implant within a patient having an SCS device or other neurostimulation system with two or more stimulation electrodes. Briefly, neurostimulation pulses are generated wherein successive pulses alternate in polarity so that a pair of electrodes alternate as cathodes. Each pulse has a cathodic amplitude sufficient to achieve cathodic capture of tissues adjacent the particular electrode used as the cathode for the pulse. The neurostimulation pulses are delivered to patient tissues using the electrodes to alternatingly capture tissues adjacent two opposing electrodes via cathodic capture to achieve a distributed virtual stimulation cathode. One advantage of this interleaved alternating-polarity multi-site stimulation technique is that additional stimulation coverage can be achieved via a single programming configuration (i.e. Stim Set) without increased energy consumption/current drain compared to otherwise standard active charge balancing. Indeed, energy savings can be achieved.

In a monophasic example, a first monophasic pulse of a pair of successive pulses is generated to achieve cathodic capture of tissues adjacent a first electrode of a pair of opposing electrodes (such as a distal electrode of a lead.) A second monophasic pulse of the pair achieves cathodic capture of tissues adjacent the second electrode of the pair of opposing electrodes (such as a middle electrode of the lead.) In this manner, the two electrodes are employed as a distributed virtual stimulation cathode. This may be achieved by switching the anode and cathode connections on a coupling capacitor of the device between alternate monophasic pulses such that the distal and middle electrodes alternate as cathodes. Moreover, by alternating the polarity of the monophasic pulses, charge balancing can be achieved.

In a biphasic example, a cathodic phase of a first biphasic pulse of a pair of successive pulses achieves capture of tissues adjacent a first (distal) electrode whereas the cathodic phase of the second biphasic pulse of the pair achieves capture of tissues adjacent the second (middle) electrode. Again, two electrodes are employed as a distributed virtual stimulation cathode. This may be achieved by switching the anode and cathode connections on the coupling capacitor of the device between alternate biphasic pulses. In addition to allowing for charge balancing, still further energy savings can achieved depending upon the frequency and pulse width of the stimulation and recharge pulses or other factors. For example, the recharge from a prior pulse can serve to precondition nerve cells near the stimulation electrode such that the tissues have a lower threshold for the next pulse. Once the threshold in the preconditioned state is determined, the system can be programmed to deliver pulses at a lower energy level for stimulation, thereby saving pulse energy. Additionally or alternatively, the pulse delivery circuit can be configured so that the active discharge phase of the prior pulse only discharges the coupling capacitor partway. Then the active discharge phase of the next biphasic pulse completes that discharge, thereby using part of the energy of the prior biphasic pulse (which would otherwise be "wasted") to drive the second biphasic pulse.

In either the monophasic or biphasic examples, the method also allows for a reduction in stimulation programming complexity by allowing a single "Stim Set" to be used to achieve capture at two electrode (e.g. middle vs. distal.) That is, the method has the effect of allowing two Stim Sets to be combined into one. As such, a clinician need not program two separate stimulation sets to achieve stimulation at two separate locations. Rather, a single Stim Set suffices. By providing for still further interleaving of pulse sequences, even more electrodes can be used as cathodes to provide still further savings in terms of overall energy consumption and/or programming complexity.

The distributed virtual cathodic stimulation techniques can be employed with a variety of leads including percutaneous leads (such as Penta™ array leads where Penta™ is a trademark of St Jude Medical), paddle leads and leads with segmented electrodes (i.e. split-rings.) For split-ring electrodes, the distributed virtual cathodic stimulation techniques can be used to selectively stimulate left and right sides of the spinal column by alternating pulse polarity.

System and method examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of SCS System

Figure 2:
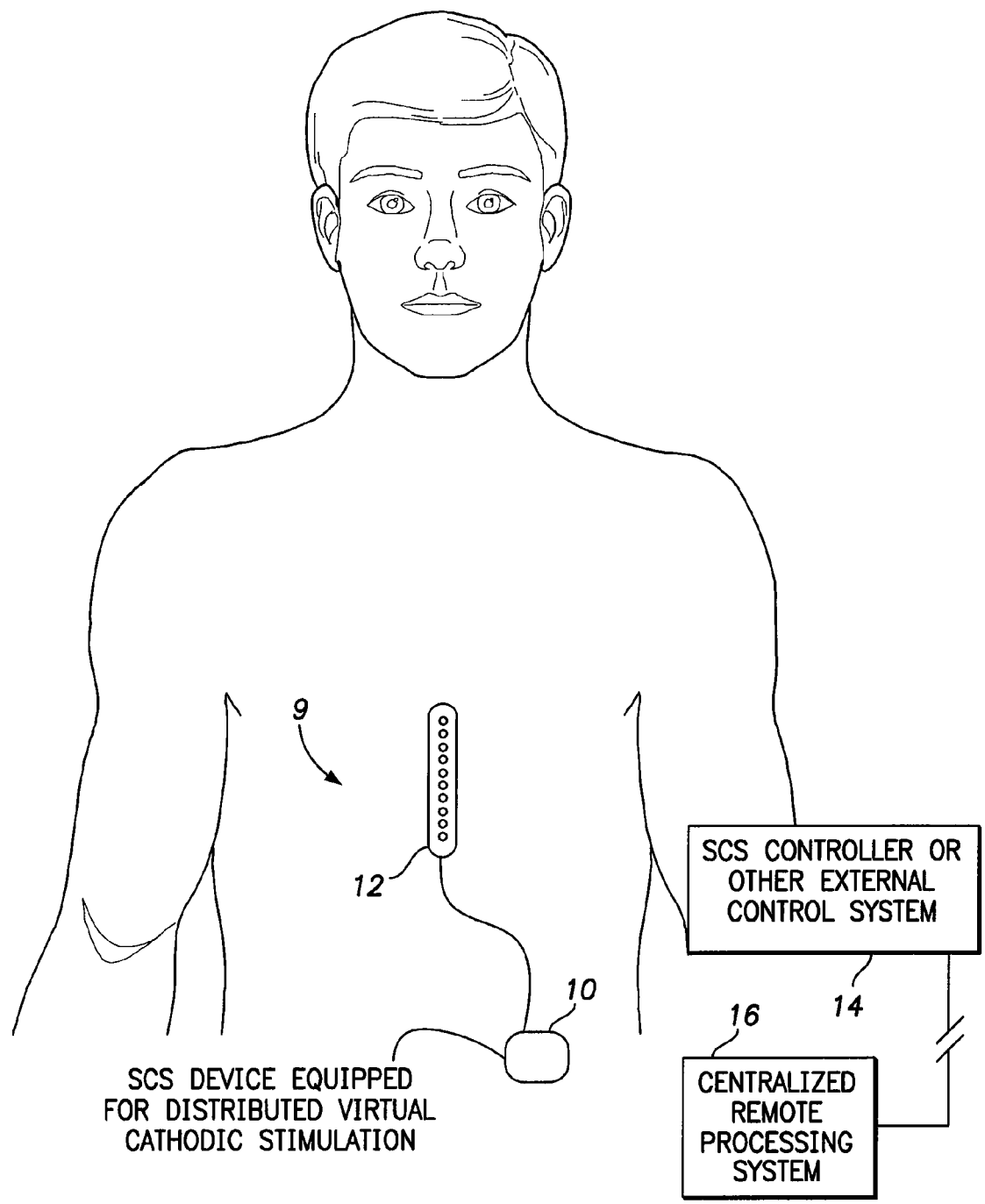
FIG. 2 illustrates pertinent components of an SCS system equipped for distributed virtual cathodic stimulation.

FIG. 2 illustrates an implantable medical system 9 having an SCS device 10 equipped for distributed virtual cathodic stimulation. The stimulation is delivered via an SCS lead or lead array 12 shown in FIG. 2 in stylized form. See FIGS. 7 and 8, discussed below, for illustrations of exemplary leads. The operation of SCS device 10 is controlled by an SCS controller 14 or other external system that programs the implanted device using one or more stimulation sets (Stim Sets) initially specified by a clinician. The stimulation sets specify SCS parameters for controlling delivery of SCS to particular nerve tissues of the patient to address the needs of the patient, such as to reduce pain or to achieve desired cardioprotective effects. As will be explained in more detail below, the SCS device then employs distributed virtual cathodic stimulation to permit fewer stimulation sets to be used to provide stimulation over a larger area of tissues or at multiple tissue locations while also limiting or reducing energy consumption from the power source of the SCS device. External system 14 may also allow the patient to directly input commands to activate, deactivate or adjust stimulation as may be needed to mitigate pain or for other reasons.

SCS controller 14 can be equipped to operate in conjunction with a centralized/remote processing system 16 for relaying information to the patient's primary care physician or to others clinicians. The centralized system may include such systems as the HouseCall™ remote monitoring system or the Merlin@home/Merlin.Net systems of St. Jude Medical. Although the example of FIG. 2 shows an SCS device 10 for stimulating the spinal cord, additional or alternative neurostimulation devices might be used, such as devices for stimulating other nerve tissues within the patient. Note that some patients might additionally have an implantable cardiac rhythm management device (CRMD) such as a pacemaker, implantable cardioverter-defibrillator (ICD) or a cardiac resynchronization device (CRT.) SCS device 10 can be equipped to operate in conjunction with the CRMD or in conjunction with other neurostimulation devices. Note also that FIG. 2 is a stylized illustration that does not necessarily set forth the precise location of the implantable components nor their relative sizes.

Exemplary Distributed Virtual Cathodic Stimulation Systems and Methods

Figure 3:
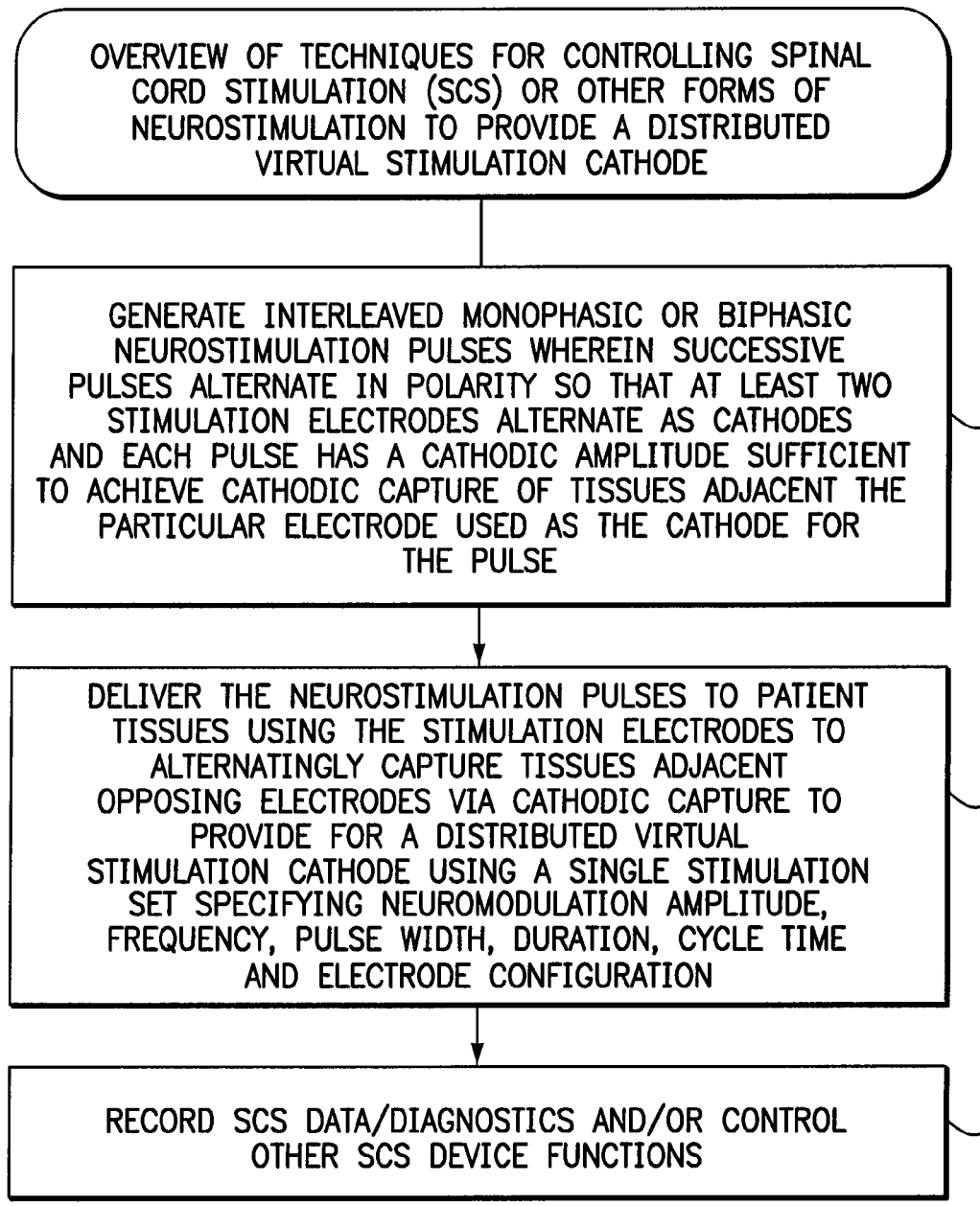
FIG. 3 is an overview of the method for controlling distributed virtual cathodic stimulation for use by the system of FIG. 2.

FIG. 3 broadly summarizes neurostimulation control procedures implemented by the system of FIG. 2 or other suitably-equipped implantable medical systems for controlling SCS or other forms of neurostimulation to provide for distributed virtual cathodic stimulation. Initially, at step 100, the system generates interleaved monophasic or biphasic neurostimulation pulses wherein successive pulses alternate in polarity so that at least two stimulation electrodes alternate as cathodes and each pulse has a cathodic amplitude sufficient to achieve cathodic capture of tissues adjacent the particular electrode used as the cathode for the pulse. At step 102, the system delivers the neurostimulation pulses to patient tissues using the stimulation electrodes to alternatingly capture tissues adjacent at least two opposing electrodes via cathodic capture to provide for a distributed virtual stimulation cathode using a single stimulation set. Exemplary neuromodulation parameters specified by the stimulation set may include: pulse amplitude (e.g., 0.1-25.5 mA); pulse frequency (e.g., 2-500 Hz); pulse width (e.g. 1-1000 μsec); SCS duration (e.g., a few seconds to several hours or other suitable interval of time); SCS cycle time (e.g., one to six "doses" per day of a given duration); and electrode configuration. The electrode configuration specifies, for example, the aforementioned distributed virtual stimulation cathode configuration while also specifying the particular electrodes to be used. At step 104, the system then records SCS data/diagnostics (such as data specifying the stimulation set used and the remaining battery power within the device) and/or controls other SCS device functions. A significant advantage of the alternating-polarity multi-site stimulation technique of FIG. 3 is that additional stimulation coverage can be achieved via a single stimulation set without increased energy consumption compared to otherwise standard active charge balancing. Indeed, in some cases, energy savings can be achieved.

Figure 4:
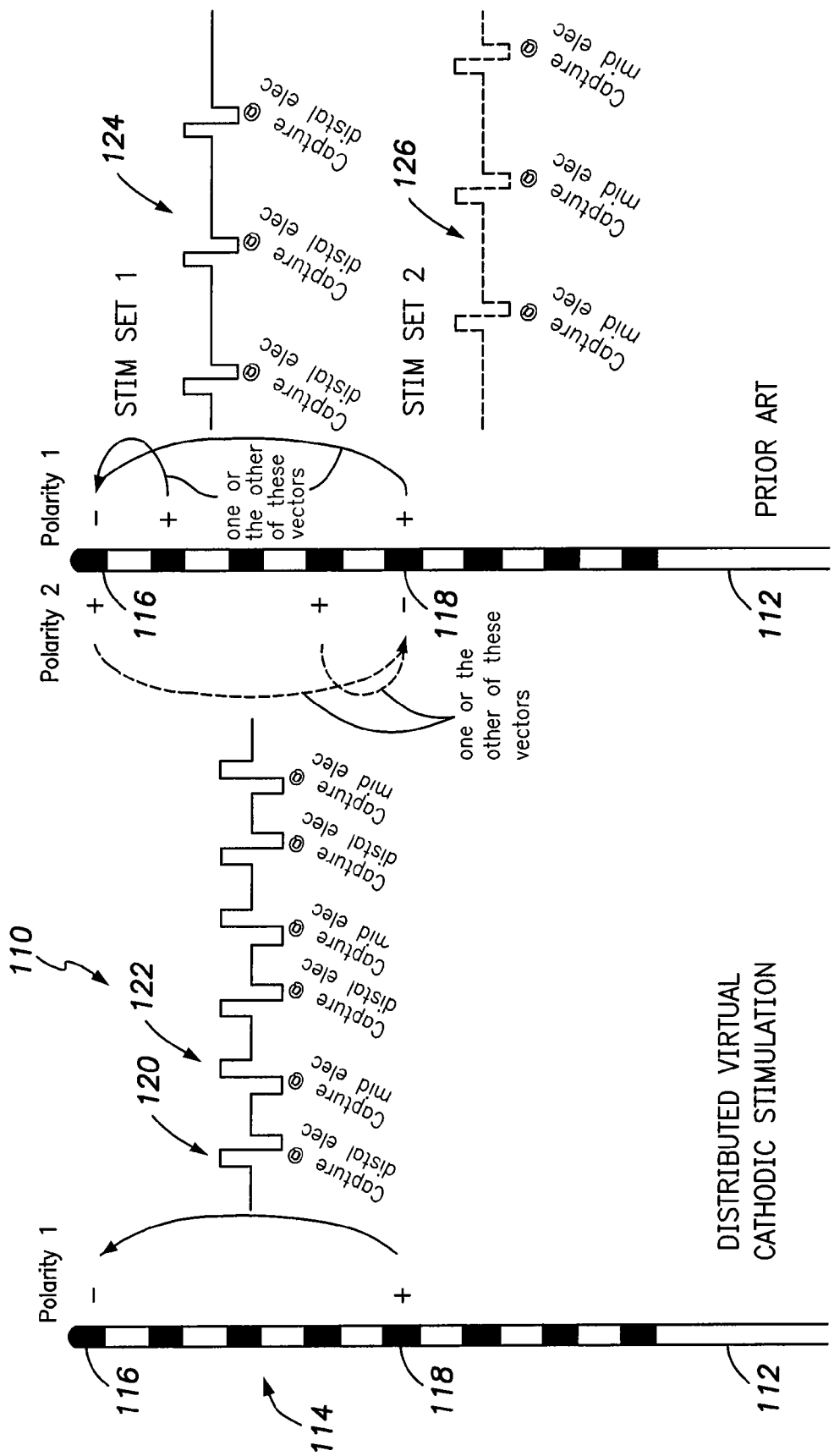
FIG. 4 illustrates exemplary SCS pulse sequences corresponding to a single stimulation set in accordance with the method of FIG. 3.

FIG. 4 illustrates an exemplary biphasic pulse sequence 110 delivered in accordance with a first stimulation set applied to a percutaneous lead 112 having a set of electrodes 114 including a distal electrode 116 and at least one middle electrode 118 (which may also be referred to herein as a proximal electrode since it is proximal relative to the distal electrode.) The other electrodes of the lead are not used in this particular example. Pulse sequence 110 includes a set of alternating or interleaved biphasic pulses where a first biphasic pulse 120 uses middle electrode 118 as its anode and distal electrode 116 as its cathode. The parameters of the pulse (including its pulse amplitude) are set such that the first, cathodic portion of the biphasic pulse stimulates or "captures" nerve tissues near electrode 116 thus triggering those nerves to fire. The second, anodic (or "recharge" portion) of the biphasic pulse stimulates nerves near electrode 118 but does not have an amplitude sufficient to capture those tissues and hence does not cause those nerves to fire. As will be explained below, this recharge phase may help precondition nerves near electrode 118 prior to the next pulse to allow for a reduction in pulse amplitude. In any case, the second biphasic pulse 122 alternates in polarity relative to the first biphasic pulse to provide cathodic stimulation/capture to tissues adjacent electrode 118 and anodic stimulation (without capture) to tissues adjacent electrode 116.

Figure 1:
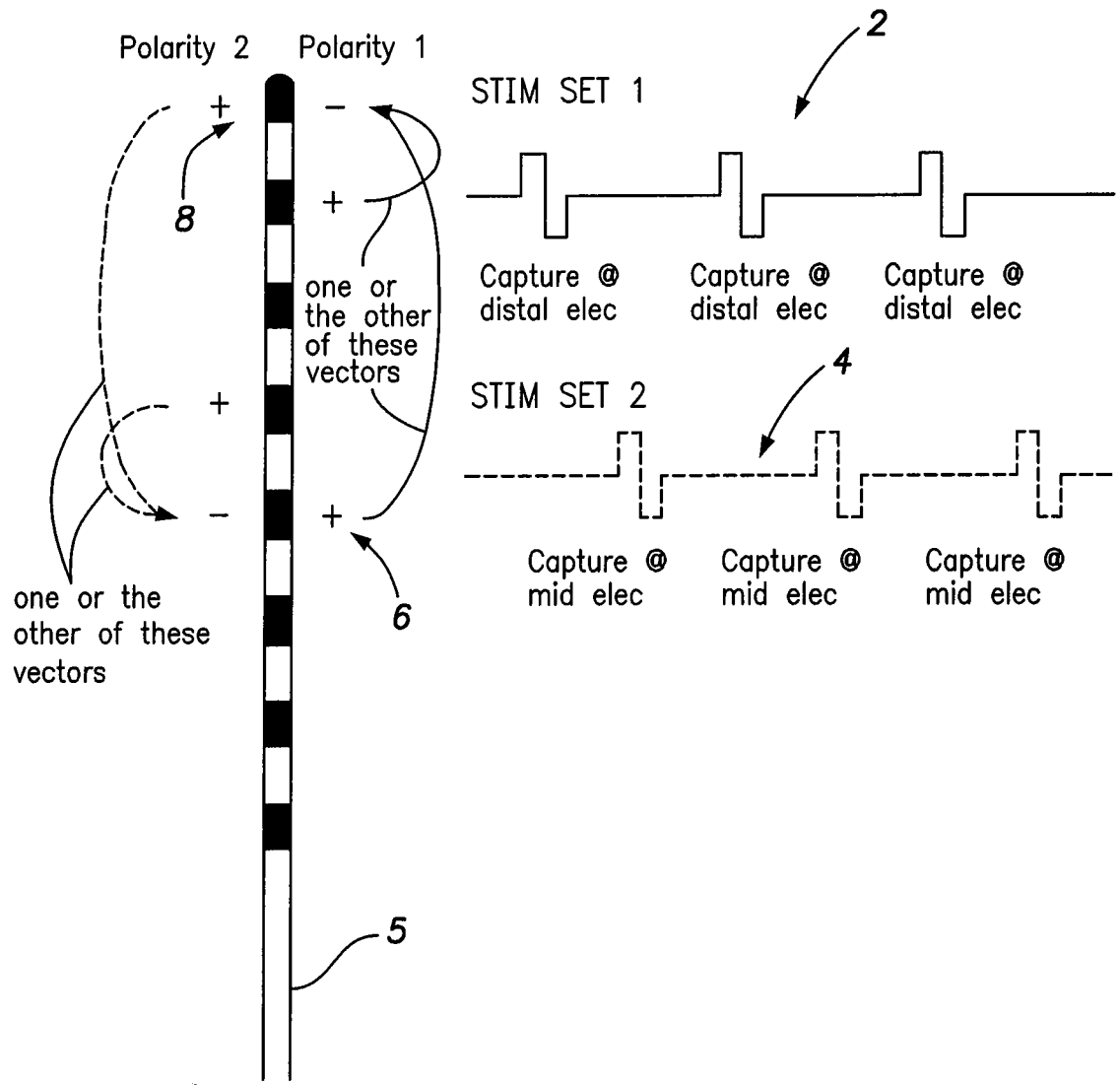
FIG. 1 illustrates exemplary SCS pulse sequences corresponding to a pair of stimulation sets in accordance with prior art.

In this manner, the first biphasic pulse achieves cathodic capture of tissues near distal electrode 116 and the second pulse achieves cathodic capture of tissues near middle electrode 118, thereby providing for what is referred to herein as distributed virtual cathodic stimulation. Each subsequent biphasic pulse alternates in polarity for the duration of a "dose" of stimulation. By alternating the polarity of consecutive biphasic pulses, the two "opposing" electrodes (116 and 118) both function as cathodes to effectively (i.e. virtually) provide for a distributed cathode. Moreover, only a single stimulation set is required to provide stimulation at the two electrode locations. For comparison, FIG. 4 also shows conventional interleaved biphasic pulse sequences 124 and 126 generated using two separate stimulation sets, as was already discussed with reference to FIG. 1.

Figure 5:
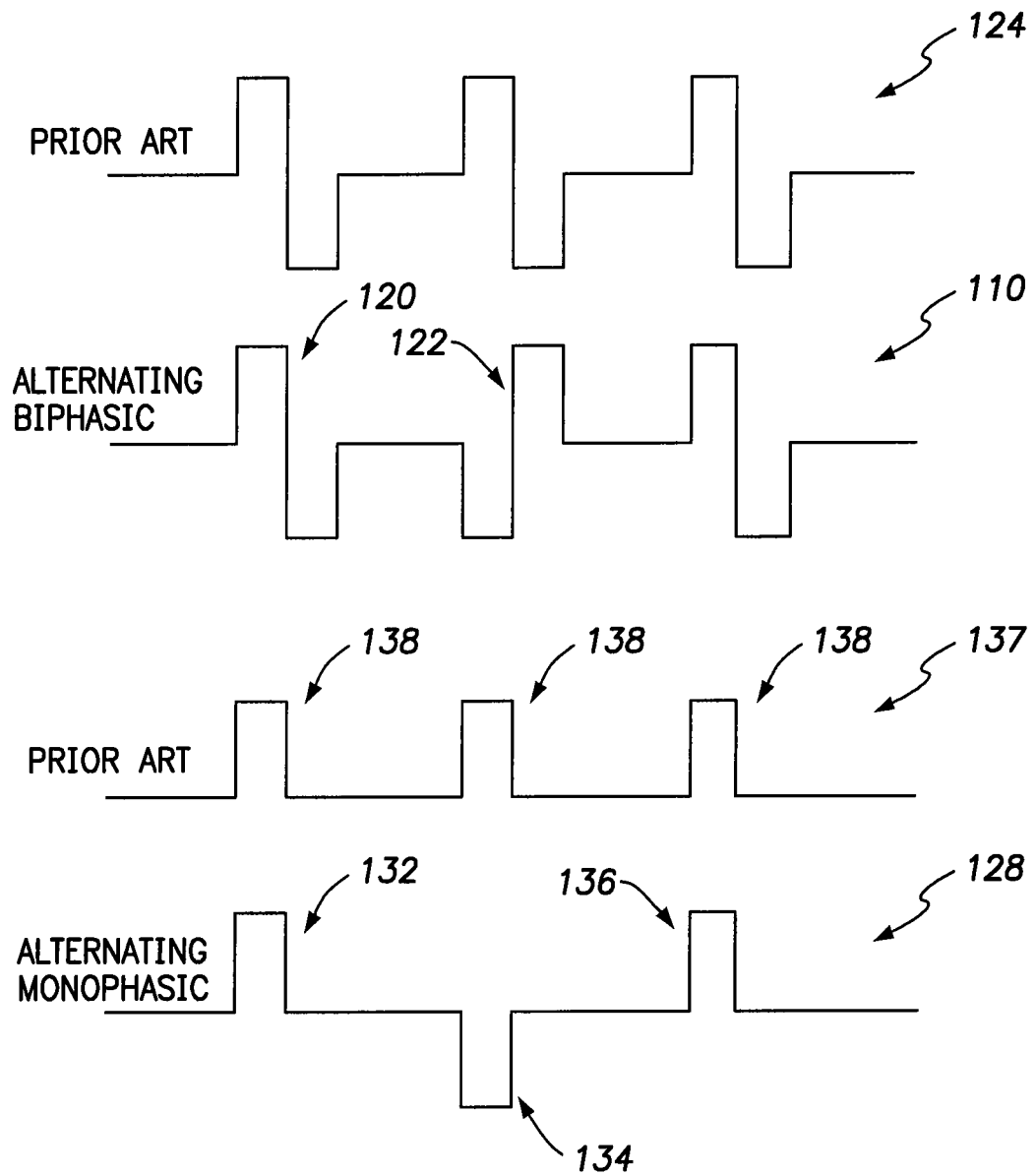
FIG. 5 illustrates exemplary SCS pulses sequences for use with the method of FIG. 3 for both monophasic and biphasic examples.

FIG. 5 illustrates alternating biphasic sequence 110 alongside conventional biphasic sequence 124 for ease of comparison. Note that the pulse sequences are shown in stylized form in this and other figures herein to emphasize the polarity of the pulses. In practice, each individual pulse phase will likely decrease in amplitude from a starting pulse amplitude as the capacitor that provides energy for the pulse discharges or subsequently recharges. FIG. 5 also illustrates an alternating monophasic pulse sequence 128 for comparison against a conventional non-alternating monophasic pulse sequence 130. The alternating monophasic sequences includes a first monophasic pulse 132 employing a first electrode (such as distal electrode 116 of FIG. 4) as its cathode to deliver stimulation at that particular electrode. The polarity then alternates so that the next monophasic pulse 134 uses a second, opposing electrode (such as middle electrode 118 of FIG. 4) as its cathode to deliver stimulation at that particular electrode. Again, this serves to provide a distributed virtual cathode using only a single stimulation set. In contrast, conventional monophasic pulse sequence 137 consists of pulses 138 of consistent polarity to, e.g., deliver cathodic stimulation at only a single electrode location (such as the distal electrode of FIG. 4.)

To provide pulse sequences of alternating polarity, an otherwise conventional circuit can be easily modified to provide logic to switch polarity as needed such as by modifying the type of circuits used within ICDs to deliver biphasic high voltage (HV) shocks. For a monophasic pulse sequence, the circuit switches the polarity of the anode and cathode connections to the coupling capacitor between each monophasic pulse such that every other monophasic pulse has the opposite polarity. For biphasic pulse sequences, the circuit switches the polarity of the anode and cathode connections to the coupling capacitor between each biphasic pulse such that every other biphasic pulse has the opposite polarity. Note that, in addition to the simplicity of using a single stimulation set to achieve cathodic stimulation at a pair opposing electrodes, energy savings can also be achieved in at least some cases. For the biphasic example, the circuit may be configured so that the active discharge phase of a first biphasic pulse only discharges the capacitor partway. Then the active discharge phase of the next biphasic pulse completes that discharge, thereby using part of the energy of the first biphasic pulse that would otherwise be "wasted" to drive the second biphasic pulse, thereby providing at least some energy savings. Additionally or alternatively, depending upon the frequency and pulse width of both stimulation and recharge pulses, the recharge from a prior biphasic pulse can serve to precondition nerve cells in vicinity of the corresponding stimulation electrode such that those tissues will then have a lower threshold for the next biphasic pulse, thereby allowing that pulse to use a lower pulse amplitude. In this regard, once the threshold in the preconditioned state is determined (e.g. during a post-implant programming session), the SCS system is then programmed to deliver pulses at the lower energy for stimulation, thereby exploiting preconditioning to achieve energy savings.

Figure 6:
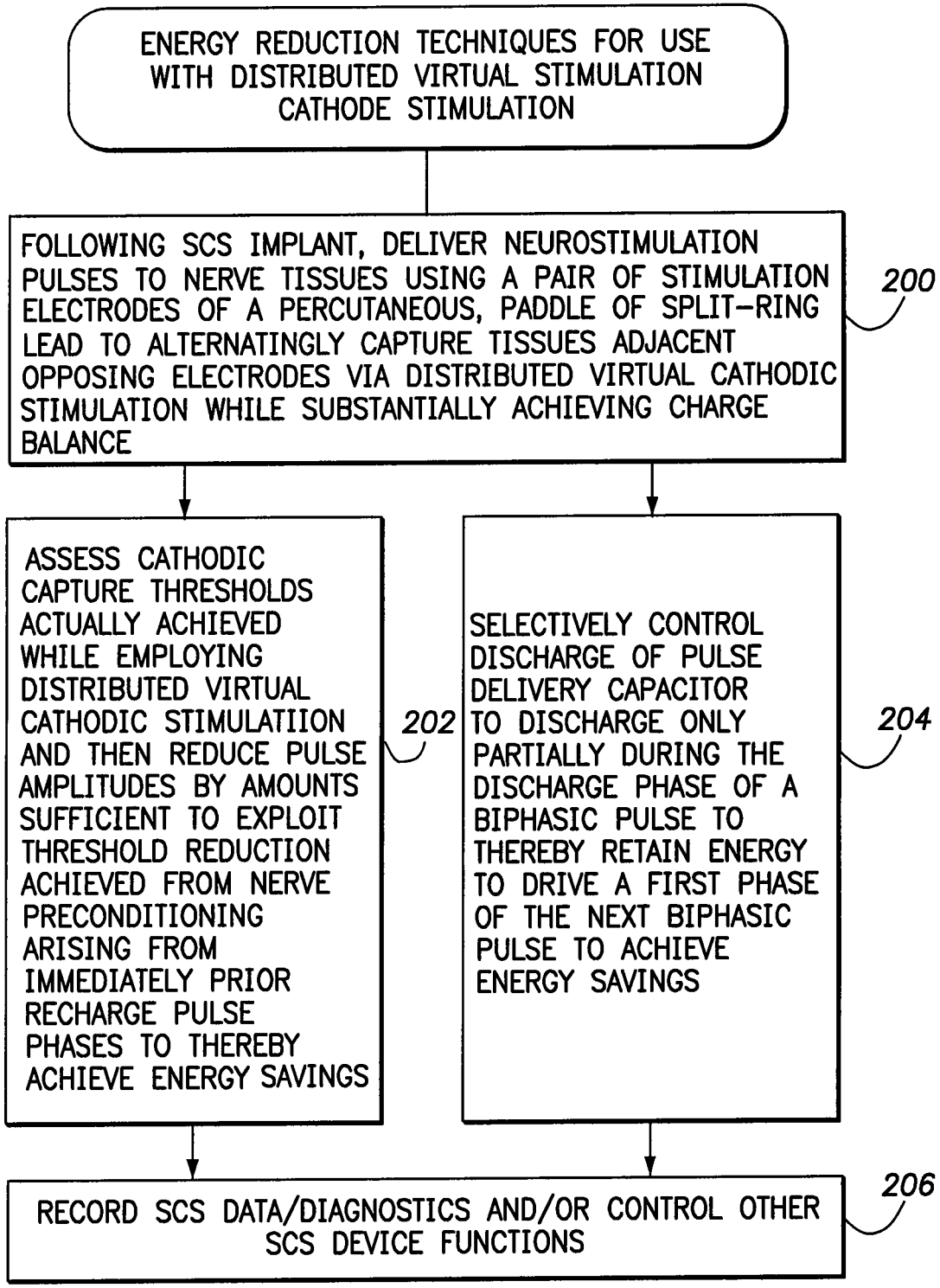
FIG. 6 summarizes aspects of the method of FIG. 3 directed to achieving energy savings.

FIG. 6 summarizes the aforementioned energy saving methods. Briefly, beginning at step 200, following SCS implant, the implantable system delivers neurostimulation pulses to nerve tissues using a pair of stimulation electrodes of a percutaneous, paddle of split-ring lead to alternatingly capture tissues adjacent opposing electrodes via distributed virtual cathodic stimulation (as already described) while substantially achieving at least partial charge balance. Then at step 202, the system assesses cathodic capture thresholds actually achieved while employing the distributed virtual cathodic stimulation of step 200 and then reduces pulse amplitudes by amounts sufficient to exploit threshold reduction achieved from nerve preconditioning arising from immediately prior recharge pulse phases to thereby achieve energy savings. Additionally or alternatively, at step 204, the system selectively controls discharge of the pulse delivery capacitor of the SCS device to discharge only partially during the discharge phase of a biphasic pulse to thereby retain energy to drive a first phase of the next biphasic pulse to thereby also achieve energy savings. That is, at least some of the energy in the capacitor is retained to help drive the next pulse. At step 206, the system records SCS data/diagnostics and/or controls other SCS device functions.

Thus, both monophasic and biphasic examples have been described where polarity alternates to achieve the benefits of a distributed virtual cathode. The advantages of alternating polarity include: (1) achieving two sites of cathodal stimulation with a single stimulation set; (2) making use of active discharge or charge balancing rather than wasting that energy to gain another stimulation pulse; (3) exploiting different effects at different levels—for example, differential effects at T2 versus T4—as this enables stimulating at both locations to obtain both effects; and (4) making use of otherwise conventional SCS electrodes or SCS patch arrays.

Figure 7:
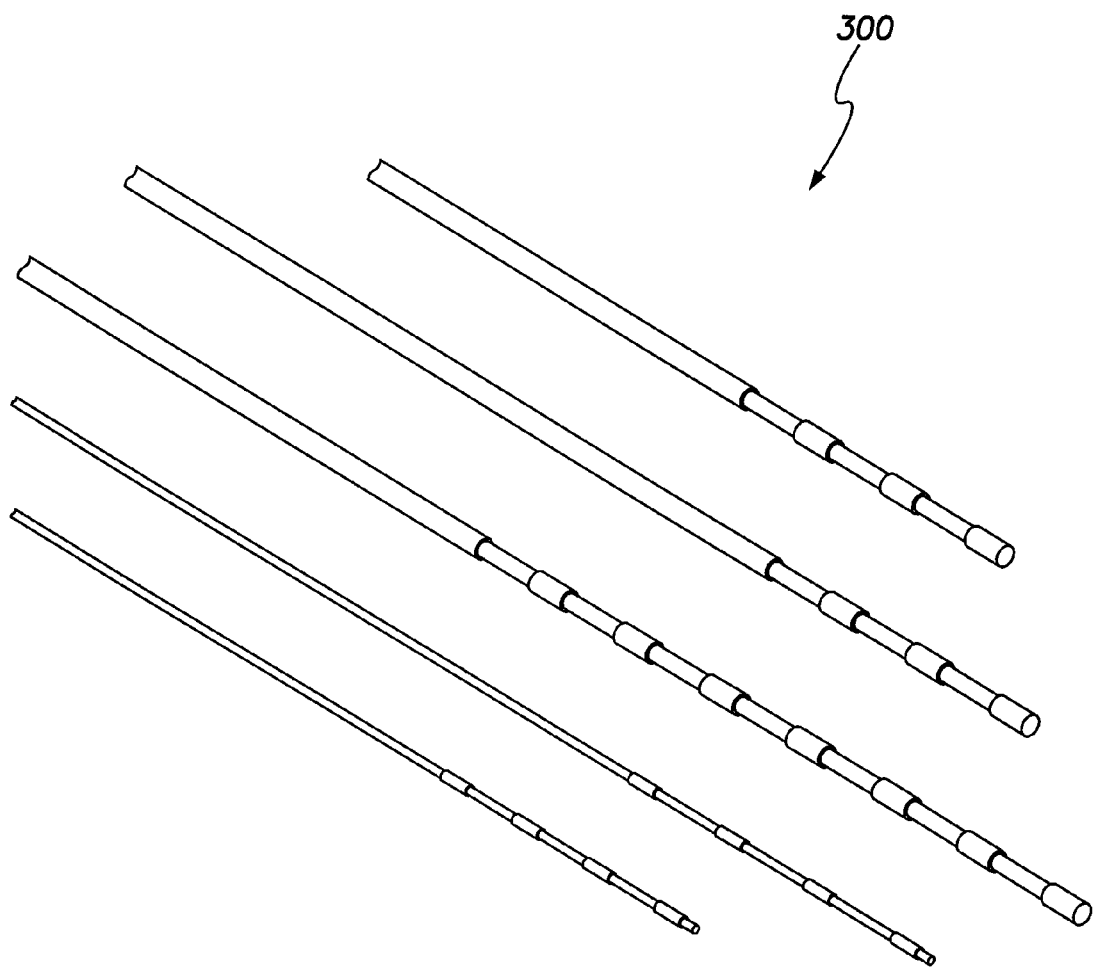
FIG. 7 illustrates exemplary percutaneous leads for use with the system of FIG. 2.
Figure 8:
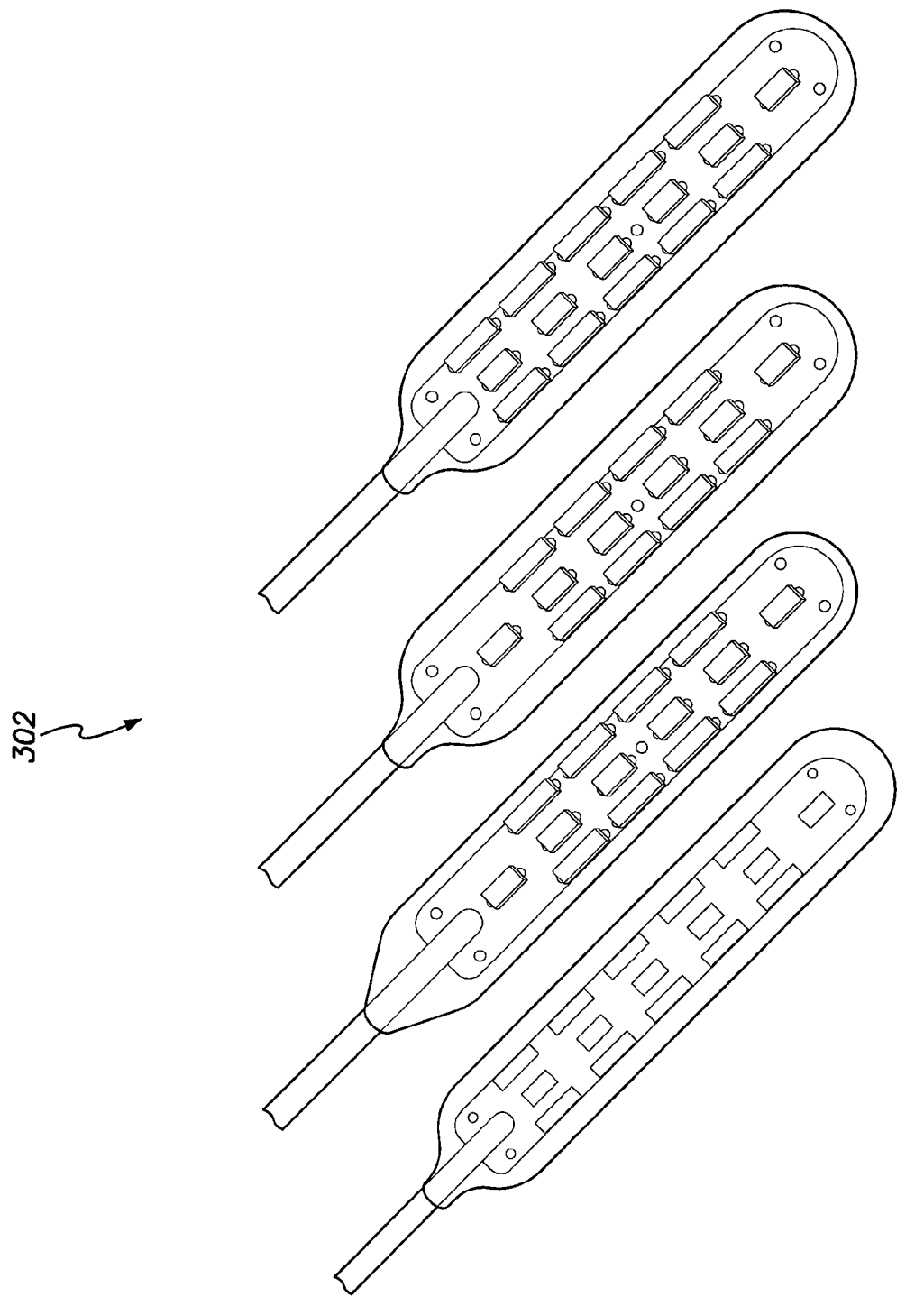
FIG. 8 illustrates exemplary paddle leads for use with the system of FIG. 2.
Figure 9:
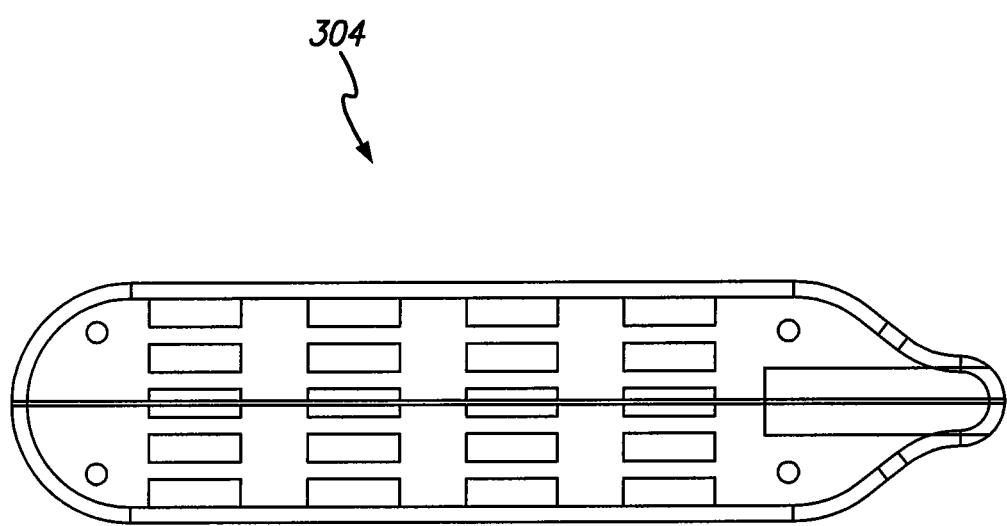
FIG. 9 illustrates exemplary Penta™ array lead for percutaneous implant for use with the system of FIG. 2.

FIG. 7 illustrates a set of linear percutaneous leads 300 of differing sizes that may be used. Note that in a linear lead having multiple electrodes, each pair of rings can be split into two or four segments. A single conductor with integrated circuit/switch can thereby allow for use of all of the combinations of all segments, or just one or two or three for each ring. FIG. 8 illustrates a set of paddle leads 302 or differing sizes that may be used. In one particular example, switching pulse polarity from a left-side pair to a right-side pair of electrodes serves to stimulate opposing sides of the spinal cord in a different time manner or by using time sequences. In yet another example, the fields can be selectively directed only to one side. The SCS device can be configured to control the selection of split segments on a ring of a suitably-configured lead. Still further, a so-called Nautilus™ lead may be exploited that includes segmented electrodes (i.e. split-rings) and electronics at the distal portion of the lead (i.e. immediately adjacent to the electrodes) along with two conductors in the lead body for connection to an IPG to control up to sixteen channels, namely four rings of four "satellite" electrodes each. FIG. 9 illustrates a Penta™ array 304 (as provided by St Jude Medical) for percutaneous implant having five columns of electrodes, each column with four electrodes. The Penta™ lead offers precise field control and broad lateral coverage. Designed to enable selective nerve fiber stimulation and predictable dermatomal activation, the lead provides enhanced control for coverage of complex, multifocal pain. In particular, the broad lateral electrode span is designed to accommodate anatomical asymmetries as well as placement variability. The five-column array is intended to provide the flexibility necessary to isolate current to specific nerve fibers. The small electrode size is designed to focus current for enhanced specificity.

Figure 10:
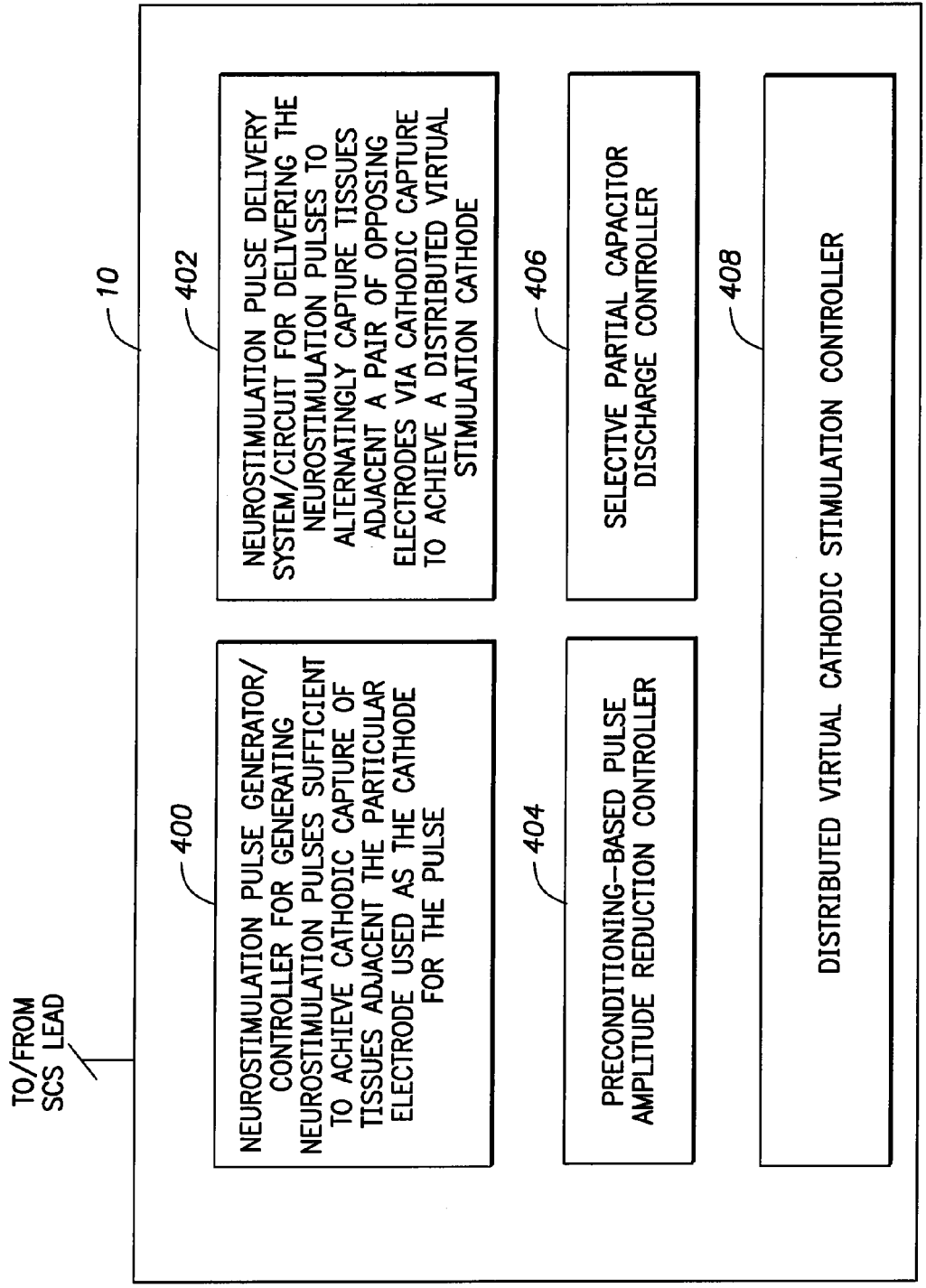
FIG. 10 is a block diagram illustrating pertinent components of the implantable SCS device of FIG. 2.

FIG. 10 summarizes components of the SCS device 10 of FIG. 2 for controlling or performing the aforementioned stimulation methods and techniques. Briefly, the device includes a neurostimulation pulse generator/controller 400 for generating neurostimulation pulses sufficient to achieve cathodic capture of tissues adjacent the particular electrode used as the cathode for the pulse. The device also includes a neurostimulation pulse delivery system/circuit 402 for delivering the neurostimulation pulses generated by generator 400 using the SCS lead(s) to alternatingly capture tissues adjacent a pair of opposing electrodes of the lead via cathodic capture to achieve a distributed virtual stimulation cathode. A preconditioning-based pulse amplitude reduction controller 404 operates to control the SCS in accordance with the aforementioned preconditioning techniques to achieve energy savings. A selective partial capacitor discharge controller 406 operates to control the SCS in accordance with the aforementioned selective capacitive discharge techniques to achieve energy savings. A distributed virtual cathodic stimulation controller 408 operates to control the various other components based on command signals received from an external system operated under clinician supervision. The various components of FIG. 10 may be implemented as separate software modules of a microcontroller, or the modules may be combined to permit a single module to perform multiple functions. In addition, some or all of these components may be implemented separately from the microcontroller, using application specific integrated circuits (ASICs) or the like.

Figure 11:
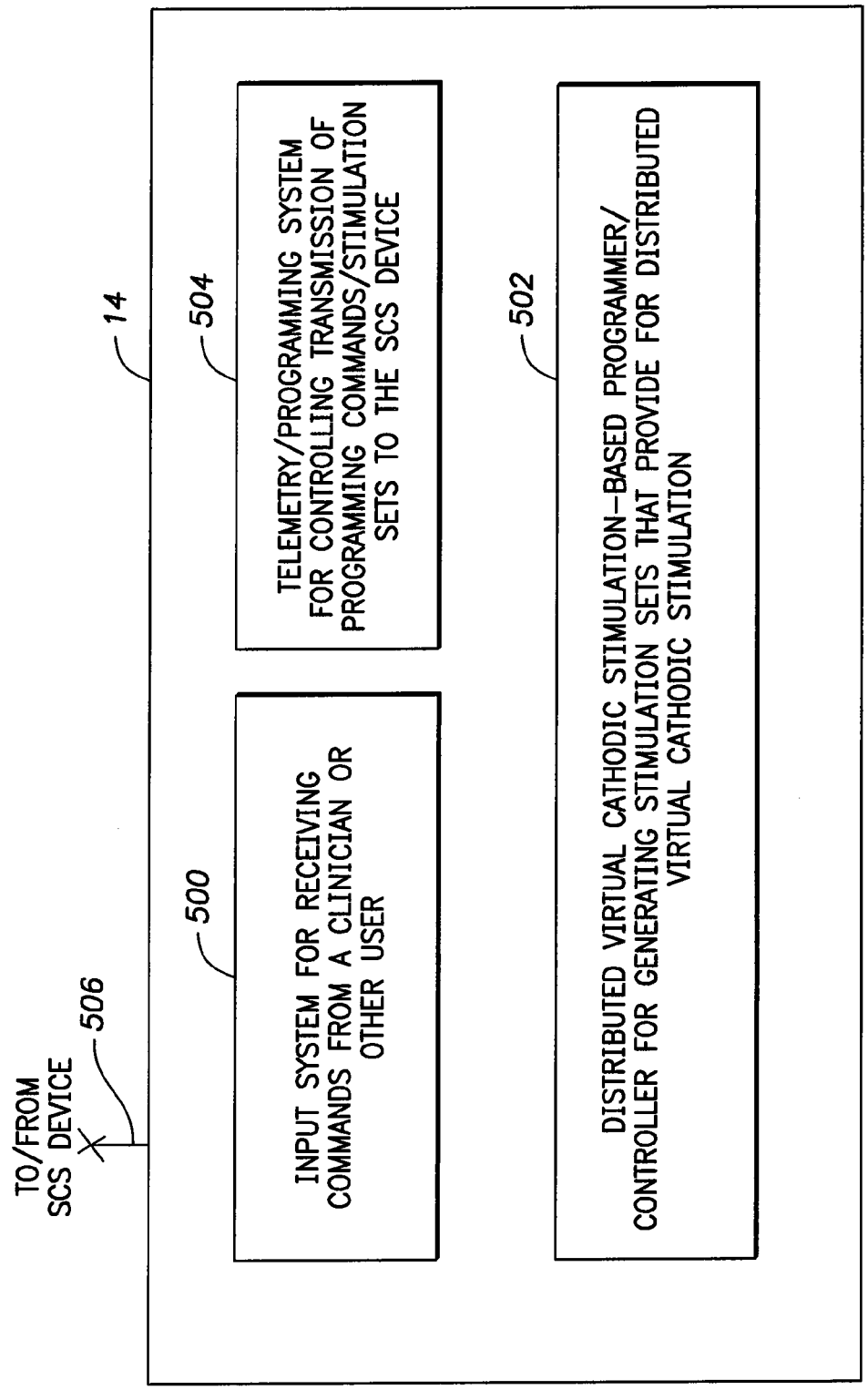
FIG. 11 is a block diagram illustrating pertinent components of the external programmer device of FIG. 2.

FIG. 11 summarizes components of the external programming device 14 of FIG. 2 for programming the aforementioned stimulation methods and techniques. Briefly, the programmer includes an input system 500 for receiving commands from a clinician or other user specifying the parameters of the stimulation to be delivered such as: neuromodulation amplitude, frequency, pulse width and electrode configuration, including an indication of whether a distributed virtual cathode stimulation set should be employed or whether otherwise conventional stimulation sets should instead be used. Assuming that distributed virtual cathodic stimulation has been selected, a distributed virtual cathodic stimulation-based programmer/controller 502 operates to generate one or more stimulation sets that provide for distributed virtual cathodic stimulation. A telemetry/programming system 504 operates to controlling transmission of programming commands/stimulation sets to the SCS device, such as a single Stim Set specifying distributed virtual cathodic stimulation. The various components of FIG. 11 may be implemented as separate software modules of a microcontroller, or the modules may be combined to permit a single module to perform multiple functions. In addition, some or all of these components may be implemented separately from the microcontroller, using ASICs or the like. An antenna 506 may be employed to transmit the commands. The antenna may be mounted, for example, within a telemetry/programming wand for manual placement over patient skin near the location of the implanted SCS device.

What have been described are various neurostimulation control techniques, particularly SCS control techniques. These techniques may be used, where appropriate, in conjunction with other neurostimulation procedures. See, for example, the neurostimulation techniques described in U.S. patent application Ser. No. 13/563,417 filed Jul. 31, 2012 of Min et al., entitled "Systems and Methods for Controlling Neurostimulation of Acupuncture Sites using an Implantable Cardiac Rhythm Management Device"; U.S. Pat. No. 7,826,899 to Ryu et al., entitled "Neurostimulation and Neurosensing Techniques to Optimize Atrial Anti-Tachycardia Pacing for Termination of Atrial Tachyarrhythmias"; and U.S. Pat. No. 7,715,915 to Ryu et al., entitled "Neurostimulation and Neurosensing Techniques to Optimize Atrial Anti-Tachycardia Pacing for Prevention of Atrial Tachyarrhythmias." See, also, U.S. Patent Application 2010/0331921 of Bornzin et al., entitled "Neurostimulation Device and Methods for Controlling Same"; U.S. Patent Application 2010/0057158 of Rodriguez et al., entitled "Neurostimulation Based on Glycemic Condition"; U.S. Pat. No. 7,164,944 to Kroll et al., entitled "Analgesic Therapy for ICD Patients." SCS is also discussed, e.g., in U.S. Pat. No. 7,099,718 to Thacker, et al. Techniques for stimulating sympathetic nerves are discussed in U.S. Pat. No. 6,937,896, to Kroll, entitled "Sympathetic Nerve Stimulator and/or Pacemaker." See, also, U.S. Patent Application 2010/0312128 of Karst et al., entitled "Systems and Methods for Monitoring Blood Partitioning and Organ Function"; U.S. Patent Application 2010/0161006 of Keel et al., entitled "System and Method for Monitoring Diastolic Function using an Implantable Medical Device." In at least some of these documents, systems and techniques are described for use with CRMDs but may be applicable for use with suitably-equipped standalone SCS devices as well.

Antiarrhythmic applications of SCS are discussed, for example, in U.S. Patent Application 2011/0137362 of Foreman et al., entitled "Activation of Cardiac Alpha Receptors by Spinal Cord Stimulation Produces Cardioprotection against Ischemia, Arrhythmias, and Heart Failure"; U.S. Pat. No. 6,134,470 to Hartlaub, entitled "Method and Apparatus for Treating a Tachyarrhythmic Patient"; and U.S. Pat. No. 7,974,693 to Ben-David et al., entitled "Techniques for Applying, Configuring, and Coordinating Nerve Fiber Stimulation." See also U.S. patent application Ser. No. 13/485,404 of Bharmi et al., filed May 31, 2012, entitled "Systems and Methods for Controlling Neurostimulation based on Regional Cardiac Performance for use by Implantable Medical Devices." Sympatholytic properties, treatments or agents are discussed, e.g., in U.S. Patent Application 2010/0114227 of Cholette, entitled "Systems and Methods for use by an Implantable Medical Device for Controlling Vagus Nerve Stimulation Based on Heart Rate Reduction Curves and Thresholds to Mitigate Heart Failure." See, also, U.S. Pat. Nos. 7,221,979 and 7,650,190 to Zhou et al., both entitled "Methods and Apparatus for the Regulation of Hormone Release." Still further, see systems and techniques described in: U.S. patent application Ser. No. 13/442,749 of Xi et al., filed Apr. 9, 2012, entitled "Systems and Methods for Controlling Spinal Cord Stimulation to Improve Stimulation Efficacy for Use by Implantable Medical Devices."

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable neurostimulation system for implant within a patient wherein the system includes at least two electrodes, the method comprising:
   generating neurostimulation pulses wherein successive pulses alternate in polarity so that at least two opposing electrodes alternate as cathodes and wherein each pulse, from the successive pulses, has a cathodic amplitude sufficient to achieve cathodic capture of tissues adjacent a particular electrode of the at least two opposing electrodes used as the cathode for the pulse; and
   delivering the neurostimulation pulses to patient tissues using the at least two electrodes to alternatingly capture tissues adjacent the at least two opposing electrodes via cathodic capture to achieve a distributed virtual stimulation cathode.

2. The method of claim 1 wherein the neurostimulation pulses are each biphasic and wherein a cathodic phase of a first biphasic pulse of a pair of successive pulses achieves capture of tissues adjacent a first electrode of the at least two opposing electrodes and wherein a cathodic phase of a second biphasic pulse of the pair of pulses achieves capture of tissues adjacent a second electrode of the at least two opposing electrodes.

3. The method of claim 2 wherein a recharge phase of the first biphasic pulse is configured to precondition nerve cells adjacent a respective electrode of the at least two opposing electrodes to achieve a lower stimulation threshold for the second biphasic pulse.

4. The method of claim 2 wherein a capacitor employed to provide pulse energy is only partially discharged during the cathodic phase of the first biphasic pulse to retain energy to provide stimulation energy for the first phase of the second biphasic pulse.

5. The method of claim 1 wherein the neurostimulation pulses are each monophasic and wherein a first monophasic pulse of a pair of successive pulses achieves cathodic capture of tissues adjacent a first electrode of the at least two opposing electrodes and a second monophasic pulse of the pair of pulses achieves cathodic capture of tissues adjacent a second electrode of the at least two opposing electrodes.

6. The method of claim 1 wherein the implantable neurostimulation system operates in conjunction with an external programmer equipped to program the implantable system using one or more simulation sets specifying an electrode configuration to be used to deliver stimulation and wherein a single stimulation set is used to program the implantable neurostimulation system to alternatingly capture tissues adjacent the different electrodes of the at least two opposing electrodes via distributed virtual cathodic stimulation.

7. The method of claim 6 wherein each stimulation set specifies a set of neurostimulation control parameters including one or more of: a neuromodulation amplitude; a neuromodulation frequency; a neuromodulation pulse width; and a neuromodulation electrode configuration.

8. The method of claim 1 wherein the successive pulses are configured to substantially achieve charge balance.

9. The method of claim 1 wherein implantable neurostimulation system includes a spinal cord stimulation (SCS) device.

10. The method of claim 1 wherein the at least two opposing electrodes include a pair of electrodes that alternate as cathodes between first, second and third successive pulses.

11. The method of claim 1 wherein the generating operation includes partially discharging a capacitor during a first pulse of a pair of successive pulses to achieve capture of tissues adjacent a first electrode of the at least two opposing electrodes and partially discharging the capacitor during a second first pulse of the pair of successive pulses to achieve capture of tissues adjacent a second electrode of the at least two opposing electrodes.

12. The method of claim 1, wherein the successive pulses include first and second pulses that achieve two sites of cathodal stimulation with a single stimulation set formed by the at least two opposing electrodes.

13. A system for use with an implantable neurostimulation system for implant within a patient wherein the system includes at least two electrodes, the system comprising:
a neurostimulation pulse generator operative to generate neurostimulation pulses wherein successive pulses alternate in polarity so that at least two opposing electrodes alternate as cathodes and wherein each pulse, from the successive pulses, has a cathodic amplitude sufficient to achieve cathodic capture of tissues adjacent a particular electrode of the at least two opposing electrodes used as the cathode for the pulse; and
a neurostimulation pulse delivery system operative to deliver the neurostimulation pulses to patient to alternatingly capture tissues adjacent the at least two opposing electrodes via cathodic capture to achieve a distributed virtual stimulation cathode.

14. The system of claim 13 wherein the neurostimulation pulse delivery system includes one or more leads.

15. The system of claim 14 wherein at least one lead is one or more of: a percutaneous lead; a percutaneous lead with five columns of electrodes, a paddle lead and a segmented electrode lead.

16. The system of claim 13 wherein implantable neurostimulation system includes a spinal cord stimulation (SCS) device.

17. The system of claim 13 wherein the at least two opposing electrodes include a pair of electrodes that alternate as cathodes between first, second and third successive pulses.

18. The system of claim 13 further comprising a capacitor, wherein the generator discharges the capacitor during a first pulse of a pair of successive pulses to achieve capture of tissues adjacent a first electrode of the at least two opposing electrodes and partially discharges the capacitor during a second first pulse of the pair of successive pulses to achieve capture of tissues adjacent a second electrode of the at least two opposing electrodes.

19. The system of claim 13 wherein the successive pulses include first and second pulses that achieve two sites of cathodal stimulation with a single stimulation set formed by the at least two opposing electrode.

20. An external system for use with an implantable neurostimulation system for implant within a patient wherein the implantable neurostimulation system includes at least two electrodes, the external system comprising:
a distributed virtual cathodic stimulation-based programming system operative to generate a stimulation set for programming the implantable neurostimulation system to provide distributed virtual cathodic stimulation; and
a telemetry system operative to control transmission of stimulation set programming commands to the implantable neurostimulation system for controlling the implantable neurostimulation system, wherein the distributed virtual cathodic stimulation is formed by generating neurostimulation pulses wherein successive pulses alternate in polarity so that at least two opposing electrodes alternate as cathodes and wherein each pulse, from the successive pulses, has a cathodic amplitude sufficient to achieve cathodic capture of tissues adjacent a particular electrode of the at least two opposing electrodes used as the cathode for the pulse.

* * * * *